United States Patent [19]

Mignot et al.

[11] Patent Number: 5,707,832
[45] Date of Patent: Jan. 13, 1998

[54] PROCESS FOR THE PREPARATION OF HUMAN FACTOR VIII AND ANALOGS OF FACTOR VIII

[75] Inventors: Gérard Mignot, Gif S/Yvette; Nicolas Bihoreau, Palaiseau; Philippe Adamowicz, Vaucresson, all of France

[73] Assignee: TM Innovation, Lyons, France

[21] Appl. No.: 384,774

[22] Filed: Feb. 7, 1995

Related U.S. Application Data

[63] Continuation of Ser. No. 970,951, Nov. 3, 1992, Pat. No. 5,422,250, which is a continuation of Ser. No. 650,580, Feb. 4, 1991, abandoned.

[30] Foreign Application Priority Data

Feb. 5, 1990 [FR] France ................................ 90 01302

[51] Int. Cl.$^6$ ............................................. C12P 21/00
[52] U.S. Cl. ........................ 435/69.6; 435/212; 530/383; 935/33; 935/34
[58] Field of Search ................................. 435/69.6, 212, 435/240.2, 240.3, 240.31; 530/383; 935/33, 34

[56] References Cited

U.S. PATENT DOCUMENTS 5,422,250  6/1995  Mignot et al. ................... 435/69.6

*Primary Examiner*—Robert A. Wax
*Assistant Examiner*—Enrique D. Longton
*Attorney, Agent, or Firm*—Blakely Sokoloff Taylor & Zafman

[57] ABSTRACT

The present invention relates to a process for the preparation of factor VIII or an analog of factor VIII by culture, in a culture medium, of cells which produce said factor VIII or analog of factor VIII and the separation of factor VIII or its analog, wherein the culture medium contains at least one derivative of a polycationic and/or polyanionic polymer.

It also relates to factor VIII or analog of factor VIII and to the complex of factor VIII or analog of factor VIII with a derivative of a polycationic and/or polyanionic polymer obtained by using this process.

8 Claims, 2 Drawing Sheets

PROCESS FOR THE PREPARATION OF HUMAN FACTOR VIII AND ANALOGS OF FACTOR VIII

This is a continuation of application Ser. No. 07/970,951 U.S. Pat. No. 5,422,250 filed Nov. 3, 1992 which is a continuation of Ser. No. 07/650,580 filed Feb. 4, 1991, now abandoned.

The present invention relates to a process for the preparation of human factor VIII and analogs of factor VIII.

Factor VIII is a blood coagulating factor which is used in the treatment of patients suffering from hemophilia A.

The factor VIII which is used in this treatment is at present essentially composed of concentrates of factor VIII obtained from human plasma by fractionation. Since then, attempts have been made to replace this source of factor VIII by a source more easily accessible and less susceptible to virus or other contaminations, thus, great effort has been made in order to obtain factor VIII by genetic engineering. The results presently obtained show that recombinant factor VIII exhibits all the characteristics of natural factor VIII and that it can be obtained under satisfactory industrial conditions.

The preparation of factor VIII by processes employing genetic engineering techniques have already been widely described notably in the following patents:

EP-A-162,067,
EP-A-182,448,
EP-A-150,735,
EP-A-157,556 and
EP-A-160,457.

In particular, the Patent EP-A-162,067 mentions the expression of factor VIII in various types of eukaryotic cells, particularly CHO cells.

The Patent EP-A-160,457 also describes the expression of factor VIII in eukaryotic cells, particularly BHK cells.

The Patents FR-A-86/08,258 and FR-A-87/04,699 describe the preparation of factor VIII using eukaryotic cells and vaccinia virus as an expression system. In order to obtain an optimum production of factor VIII, the culture medium contains von Willebrand factor.

By way of eukaryotic cells, the Patent EP-A-253,455 also suggests the use of yeasts for preparing factor VIII.

Several analogs of factor VIII have also been proposed. Among the patents covering these derivatives, the following can particularly be mentioned:

WO-A-86/06,101,
EP-A-232,112,
WO-A-87/07,144,
WO-A-88/00,381,
EP-A-265,778,
EP-A-294,910 and
EP-A-303,540.

These analogs of factor VIII exhibit various advantages over "natural factor VIII" and, like it, can be obtained by genetic engineering techniques.

The processes which are used at present preferably employ eukaryotic cells which express factor VIII, these being either cells which have integrated one or more coding sequences for factor VIII in the chromosome, or cells which incorporate virus vectors that express factor VIII.

This type of technology is extensively described in the aforementioned patents and will not be redescribed here in detail. Mention will simply be made of cells which express factor VIII or an analog of factor VIII.

By analog of factor VIII, there is understood a molecule which has the activity of factor VIII and which is obtained from factor VIII by deletion of some amino acids or a molecule of factor VIII which has undergone certain potential mutations but which nevertheless retains the principal activity of factor VIII.

As described in the Patents WO-87/04,187, FR-A-8,608, 258 and FR-A-87/04,699, it may be useful, in order to optimize the preparation of factor VIII or of an analog of factor VIII, to envisage the addition into the cell culture medium of von Willebrand factor or of phospholipid.

It has in effect been shown that the presence of this von Willebrand factor in the culture medium made it possible to stabilize factor VIII and to considerably improve the yield.

For similar reasons to those that have just been mentioned, the von Willebrand factor used is obviously a recombinant von Willebrand factor in order to avoid any risk of contamination. This requires the use of an additional step in the production and an increase in the cost of the process for the preparation of factor VIII, notably, a doubling of the price.

It will therefore be useful to have a process for the preparation of factor VIII which does not require the use of von Willebrand factor but which nevertheless results in high yields of factor VIII.

The aim of the present invention is precisely to propose a solution to this problem.

More particularly, the present invention relates to a process for the preparation of factor VIII or an analog of factor VIII by culture, in a culture medium, of cells which produce said factor VIII or analog of factor VIII and the separation of factor VIII or its analog, wherein the culture medium contains at least one derivative of a polycationic and/or polyanionic polymer.

Among the analogs of factor VIII, mention can be made particularly of factor VIII delta 2 which corresponds to a deletion of amino acids 771 to 1666 of factor VIII and whose preparation is more particularly described in the Patent EP 303,540.

The polymers in accordance with the present invention are preferably derivatives of polyosidic polymers notably polysaccharides.

These polymers are preferably sulfated.

This type of polymer is known, they are especially products obtained by bacterial fermentation, for example, dextran, or they are extraction products such as mucopolysaccharides of the type heparin, heparin of low molecular weight or heparinoids, or dermatan sulfate or heparan sulfate.

Hydroxyethylstarch sulfate can also be used by way of polymer.

These compounds are particularly useful in view of their low cost and their availability.

The polymer used in accordance with the present invention has a molecular weight between 1000 and 1,000,000.

According to a particular embodiment of the invention, the polymer used is a sulfated dextran. The degree of sulfation of this sulfated dextran is of the order of 0.5% to about 18% by weight of sulfur and preferably from 10 to about 18%.

Sulfated dextrans of very diverse molecular weight can be used in accordance with the invention. Their weight can thus vary from 5000 to 700,000 Daltons.

Using an advantageous embodiment of the invention, the polymer derivative which can be used is coupled with a divalent metallic ion. The following ions can be mentioned, in a non-restrictive manner, $Ca^{2+}$, $Mg^{2+}$, $Mn^{2+}$, $Cu^{2+}$, the $Ca^{2+}$ ions being preferred.

The presence of a polycationic and/or polyanionic polymer, in accordance with the invention, in a culture medium which is suitable for the production of factor VIII or analog of factor VIII and exempt of von Willebrand factor, results in yields of factor VIII or analogs of factor VIII which are significantly higher than those obtained in a medium containing neither von Willebrand factor nor a polymer in accordance with the invention.

Thus, it emerges from the experiments carried out in accordance with the process of the present invention and which are described in the examples below, that it is possible, using a culture medium containing sulfated dextran of a molecular weight of 500,000, to obtain large quantities of factor VIII delta 2 determined by two different methods, one based on an immuno-enzymatic method, using anti-factor VIII monoclonal antibodies, and the other by a physico-chemical method such as PAGE-SDS analysis under reducing or non-reducing conditions, which reveals a major band at 165 KDa which represents the major form of factor VIII delta 2 expressed in the absence of bovine serum.

Molecular weights (5000, 8000, 15,000, 50,000, 500,000 Da) gave essentially equivalent results for the expression of factor VIII.

The culture medium, supplemented with a polycationic and/or polyanionic polymer, may naturally contain other agents which are likely to favor the production of factor VIII. They may be antiprotease agents and/or calcium chloride known for its stabilizing properties.

Under these conditions, it has been shown, for a culture medium supplemented with 1000 mg/l of sulfated dextran and 2 mmoles of calcium chloride (1 mM in the minimal medium+1 mM added), that it is possible to accumulate in 24 hours, quantities of factor VIII delta 2, measured by an immuno-enzymatic method, which are 6 to 7 times higher than the quantity accumulated in the absence of exogenous von Willebrand factor.

The molecule of factor VIII, complete or deleted in the B region, has the characteristic of possessing high densities of very localized charges which create positively and negatively charged poles capable of binding to Coulomb forces (ionic type interactions) to polyanions and polycations respectively. The beneficial effect of sulfated dextran on the production of factor VIII can be explained by the existence of such interactions between the sulfate groups of dextran and the basic amino acids of factor VIII. This stabilization of the complete or deleted molecule of factor VIII is furthermore to be associated with an increase in the rate of expression of factor VIII or derivative of factor VIII.

There is probably formation of a complex between the complete or deleted molecule of factor VIII and at least one of the molecules of the polycationic and/or polyanionic derivative employed in the culture medium.

The present invention also relates to this complexed form of factor VIII or derivative of factor VIII.

This stabilized form of factor VIII or one of its derivatives can exhibit great usefulness in particular for the storage of said factor VIII or derivative of factor VIII during the production process or following it. Furthermore, when factor VIII or one of its derivatives is complexed with sulfated dextran which is a freeze-drying agent, it can be expected that the complex thus formed will also exhibit a good freeze-drying capacity.

The presence of sulfated dextran can therefore at the same time have a stabilizing effect towards factor VIII and also a stimulating effect on the expression of factor VIII through interaction at the level of cell membranes.

The culture medium used in accordance with the invention is preferably a culture medium without serum, derived especially from recombinant human insulin and which may contain other exogenous proteins.

These proteins are preferably used at a concentration of the order of 4 mg/l.

The cells used for the production of factor VIII or analog of factor VIII are preferably mammalian cells and more particularly recombinant CHO cells which express factor VIII or analog of factor VIII in a continuous manner.

These cells are transfected with an integration vector containing the cDNA of factor VIII or derivative of factor VIII in the presence of elements which are required for its expression in eukaryotic cells and a segment of DNA which favors integration of the vector in cellular DNA. It is thus possible to use by way of expression vector for factor VIII, pTG 1020, and for factor VIII delta 2, pTG 1509 which are described in the Patent EP 0,303,540 as well as expression vectors of similar construction. The strains for the plasmids pTG 1509 and pTG 1020 have been deposited under the No. I-679 and I-681 in the National Collection of Microbial Cultures.

The transfection of CHO cells with these integration vectors is carried out according to the technique described in Patent EP 0,303,540 and will not be repeated here.

The process according to the present invention therefore exhibits several advantages.

It allows factor VIII or an analog of factor VIII to be obtained by genetic engineering with an optimized yield.

It does not require the presence of von Willebrand factor in the culture medium and thus lead to a significant gain in time and in cost for the industrial production of factor VIII or analog of factor VIII.

Finally, the type of polymer used in accordance with the invention does not carry any risk of virus or other contamination, it is not very costly, and it is easy to obtain for the specialist.

The present invention also relates to factor VIII or analog of factor VIII obtained according to the process of the invention.

Other advantages and characteristics of the present invention will emerge from the non-restrictive examples thereof given below.

EXPERIMENTAL SECTION

Figure 1:
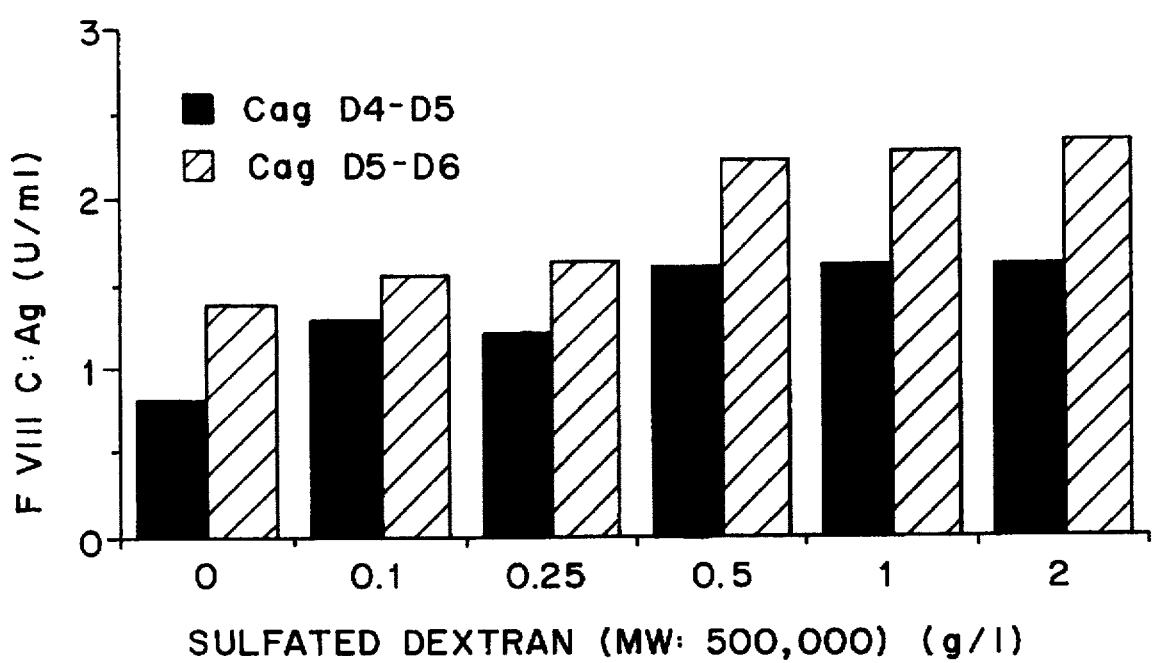
FIG. 1 shows the dose effect of sulfated dextran on the expression of factor VIII.

Studies of the effect of sulfated polyosidic polymers on the expression of factor VIII delta 2 were carried out using the clone CHO TG2307-11.

EXAMPLE 1

Study of the Effects of Dextran T 2000 on the Expression of Factor VIII Delta 2

In a first step, by way of reference, the effects of dextran T 2000 (PHARMACIA MW: 2,000,000 Da) were evaluated. Table 1 below summarizes the results obtained in comparison with a medium containing 2 U/ml of recombinant von Willebrand factor.

Dextran T 2000 (non-sulfated) has little effect on the expression of factor VIII delta 2 in the absence of serum and recombinant von Willebrand factor.

Consequently, the dextran matrix consisting of nonsubstituted glucopyranosyl units do not interfere with the molecule of factor VIII delta 2.

TABLE I

STUDY OF THE EFFECTS OF THE ADDITION OF DEXTRAN T 2000 PRODUCTION MEDIA FOR FACTOR VIII DELTA 2 CLONE CHO TG 2307-11-3

| PRODUCTION MEDIA | APTT mU/ML D3-D4 | AVERAGE |
|---|---|---|
| H/I HUM INS 4 mg/L + | 1000 | 1000 |
| 2 U vWFrec CNTS/ML | 1000 | |
| H/I HUM INS 4 mg/L + | 250 | 265 |
| 0 mg/L DEXTRAN T 2000 | 280 | |
| H/I HUM INS 4 mg/L + | 250 | 300 |
| 1000 mg/L DEXTRAN T 2000 | 320 | |
| H/I HUM INS 4 mg/L + | 265 | 280 |
| 2000 mg/L DEXTRAN T 2000 | 300 | |

PASSAGE P15 AFTER THAWING AND P12 IN MEM HT
GROWTH (37) AND TESTS FOR PRODUCTION (35C) IN 6-WELL PLATES
CHANGE OF MEDIUM EVERY 24 HOURS
HUMAN INS ELI LILLY 319KK9B
DEXTRAN T 2000 (PHARMACIA): MW 2,000,000 Da

EXAMPLE 2

Study of the Effects of Sulfated Polymers on the Expression of Factor VIII Delta 2
1) Sulfated Dextran A dose-effect of sulfated dextran (PHARMACIA MW: 500,000) was carried out. Table 2 below also shows the data obtained with the same medium containing two units of recombinant von Willebrand factor.

Under these conditions it is possible, in a production cycle lasting from the 3rd to the 6th day with daily renewal of medium, to obtain, during one of the periods of incubation (5th to 6th day), quantities of factor VIII delta 2, determined by ELISA, which are at most equivalent to ⅔ of the activities accumulated in the presence of two units/ml of recombinant von Willebrand factor.

These activities represent, furthermore, about 2 to 3 times the level of activities obtained in a medium not containing either recombinant von Willebrand factor or sulfated dextran and in the absence of phospholipids.

2) Bovine Heparin (KABI VITRUM)

The results of a study of a dose-effect of bovine heparin are summarized in Table 3.

During the first cycles of production, heparin shows a very limited, even non-existent, effect on the expression of factor VIII delta 2. During the last day of incubation D5-D6, a very weak dose-effect relationship can be shown.

TABLE 2

STUDY OF THE EFFECTS OF THE ADDITION OF DEXTRAN SULFATE TO THE PRODUCTION MEDIA FOR FACTOR VIII DELTA 2 CLONE CHO TG 2307-11-3

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 |
|---|---|---|---|---|---|---|
| MEM HT 10 FCS ND | 570 | — | — | 11700 | 720 | 15900 |
|  | 608 |  | 651 | 9000 | 760 | 16400 |
| H/I HUM INS 4 mg/L + | 249 |  | 467 | 7300 | 500 | 10000 |
| 2 U vWFrec CNTS/ML | 280 |  | 409 | 7500 | 510 | 8400 |
| H/I HUM INS 4 mg/L + | ND | 2800 | ND | 2200 | ND | 4200 |
| 250 mg/L DS |  | 6000 |  | 1600 |  | 4500 |
| H/I HUM INS 4 mg/L + | ND | 4500 | ND | 4600 | ND | 4600 |
| 500 mg/L DS |  | 3100 |  | 4300 |  | 4300 |
| H/I HUM INS 4 mg/L + | ND | 3400 | ND | 4800 | ND | 5000 |
| 1000 mg/L DS |  | 3000 |  | 4700 |  | 6400 |
| H/I HUM INS 4 mg/L + | ND | 3800 | ND | 5000 | ND | 6300 |
| 2000 mg/L DS |  | 3400 |  | 5000 |  | 6500 |

PASSAGE P24 AFTER THAWING AND P21 IN MEM HT FCS ND 701121
GROWTH (37) AND TEST FOR PRODUCTION (35C) IN 6-WELL PLATES NUNC
CHANGE OF MEDIUM EVERY 24 HOURS
HUMAN INS ELI LILLY 319KK9B
6-WELL PLATES NUNC
DS: DEXTRAN SULFATE MW: 500,000 PHARMACIA 17% S
ND: CANNOT BE DOSED BECAUSE OF THE ANTICOAGULATING ABILITY OF SULFATE D DEXTRAN

TABLE 3

STUDY OF THE EFFECTS OF THE ADDITION OF BOVINE HEPARIN TO THE PRODUCTION MEDIA FOR FACTOR VIII DELTA 2 CLONE CHO TG 2307-11-3

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 |
|---|---|---|---|---|---|---|
| MEM HT 10 FCS ND | 1500 | 18530 | 1920 | 35000 | 5000 | 36000 |
|  | 1570 | 14920 | 2230 | 36000 | 2830 | 27300 |
| H/I HUM INS 4 mg/L + | 900 | 11410 | 1220 | 24400 | 1870 | 28900 |

TABLE 3-continued

STUDY OF THE EFFECTS OF THE ADDITION OF BOVINE HEPARIN TO THE
PRODUCTION MEDIA FOR FACTOR VIII DELTA 2 CLONE CHO TG 2307-11-3

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 |
|---|---|---|---|---|---|---|
| 2 U vWFrec CNTS/ML | 1050 | 11400 | 1070 | 29300 | 2100 | 32500 |
| H/I HUM INS 4 mg/L | 213 | 1850 | 130 | 2630 | 142 | 2000 |
|  | 148 | 1460 | 110 | 3050 | 125 | 1100 |
| H/I HUM INS 4 mg/L HEPARIN 10 U/ML | ND | 2060 | ND | 1110 | ND | 800 |
|  |  | 1300 |  | 1560 |  | 1100 |
|  |  | 2950 |  | 1850 |  | 2400 |
| H/I HUM INS 4 mg/L HEPARIN 20 U/ML | ND | 2430 | ND | 1650 | ND | 2400 |
|  |  | 2300 |  | 2060 |  | 3000 |
|  |  | 2480 |  | 1940 |  | 3400 |
| H/I HUM INS 4 mg/L HEPARIN 40 U/ML | ND | 2500 | ND | 2170 | ND | 3500 |
|  |  | 3620 |  | 3220 |  | 5300 |
|  |  | 3120 |  | 2350 |  | 4800 |
| H/I HUM INS 4 mg/L HEPARIN 80 U/ML | ND | 3120 | ND | 2850 | ND | 4000 |
|  |  | 3680 |  | 3400 |  | 5300 |
|  |  | 3920 |  | 3400 |  | 5000 |

PASSAGE P24 AFTER THAWING AND P21 IN MEM HT FCS ND 701121
GROWTH (37) AND TEST FOR PRODUCTION (35C) IN 6-WELL PLATES NUNC
CHANGE OF MEDIUM EVERY 24 HOURS
HUMAN INS ELI LILLY 319KK9B
BOVINE HEPARIN KABI VITRUM
ND: CANNOT BE DOSED BECAUSE OF THE ANTICOAGULATING ABILITY OF HEPARIN

EXAMPLE 3

The effects of combining sulfated dextran and calcium chloride on the rate of expression of factor VIII delta 2 have also been evaluated, in comparison with control media containing either 10% fetal calf serum, or 2 U/ml von Willebrand factor, or only human insulin which is used in the composition of all the media without serum used in the experiment.

The results obtained are shown in Table 4 below.

It emerges that for the values which are close to the optimum, that is to say 1000 mg/l sulfated dextran and 2 mM calcium chloride (1 mM in minimal medium+1 mM added), it is possible to accumulate in 24 hours between 20 and 21 units of antigen of factor VIII delta 2, in other words, about ⅔ of the quantity accumulated in the presence of 2 units of recombinant von Willebrand factor (2 U/ml) and up to 7 times the quantity accumulated in the absence of fetal calf serum or von Willebrand factor.

It is also observed that in the absence of fetal calf serum or recombinant von Willebrand factor, the activities accumulated in 24 hours are never greater than 3 units/ml and are 2.27 units/ml on average, that is to say, very significantly lower than the activities accumulated in the presence of optimum quantities of sulfated dextran.

TABLE 4

STUDY OF THE EFFECTS OF THE ADDITION OF DEXTRAN SULFATE TO THE PRODUCTION MEDIA FOR FACTOR VIII DELTA 2
CLONE CHO TG 2307-11-3 DOEHLERT DEXTRAN SULFATE (0–2000 mg/L)/CaCl₂ (2–11 mM)

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| MEM HT 10% FCS ND | 1500 | 18500 | 1920 | 34000 | 2830 | 28000 | 1310 | 30700 |
|  | 1600 | 14900 | 2230 | 35000 | 5000 | 36000 | 1850 | 35000 |
| H/I HUM INS 4 mg/L + 2 U vWFrec CNTS/ML | 1050 | 11400 | 1220 | 24400 | 1870 | 28900 | 1750 | 33700 |
|  | 900 | 11400 | 1070 | 29300 | 2100 | 32500 | 1370 | 26700 |
| H/I HUM INS 4 mg/L | 210 | 1850 | 130 | 2650 | 125 | 1130 | 142 | 3000 |
|  | 150 | 1460 | 110 | 3050 | 142 | 1900 | 124 | 3170 |
| *H/I HUM INS 4 mg/L + 1000 mg/L DS Ca 5 mM | ND | 856 | ND | 8000 | ND | 5000 | ND | 5700 |
| H/I HUM INS 4 mg/L + 1000 mg/L DS Ca 10 mM | ND | 980 | ND | 6150 | ND | 4700 | ND | 3920 |
|  |  |  |  |  |  | 6000 |  | 4980 |
| H/I HUM INS 4 mg/L + 1000 mg/L DS Ca 1 mM | ND | 1350 | ND | 8400 | ND | — | ND | 21610 |
|  |  |  |  |  |  | — |  | 20550 |
| H/I HUM INS 4 mg/L + 1866 mg/L DS Ca 7.5 mM | ND | 1380 | ND | 8550 | ND | 10700 | ND | 12000 |
|  |  |  |  |  |  | 8000 |  | 10520 |
| H/I HUM INS 4 mg/L + 134 mg/L DS Ca 2.5 mM | ND | 655 | ND | 6600 | ND | 9900 | ND | 15585 |
|  |  |  |  |  |  | 10150 |  | 15410 |
| H/I HUM INS 4 mg/L + | ND | 250 | ND | 6700 | ND | 7800 | ND | 11260 |

TABLE 4-continued

STUDY OF THE EFFECTS OF THE ADDITION OF DEXTRAN SULFATE TO THE PRODUCTION MEDIA FOR FACTOR VIII DELTA 2
CLONE CHO TG 2307-11-3 DOEHLERT DEXTRAN SULFATE (0–2000 mg/L)/CaCl₂ (2–11 mM)

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| 134 mg/L DS Ca 7.5 mM | | | | | | 10150 | | 13900 |
| H/I HUM INS 4 mg/L + 1866 mg/L DS Ca 2.5 mM | ND | 1420 | ND | 6300 | ND | 9700 10950 | ND | 15510 14120 |

PASSAGE P24 AFTER THAWING AND P21 IN MEM HT FCS ND 701121
GROWTH (37) AND TEST FOR PRODUCTION (35C) IN 6-WELL PLATES NUNC
CHANGE OF MEDIUM EVERY 24 HOURS
HUMAN INS ELI LILLY 319KK9B
6-WELL PLATES NUNC
DS: DEXTRAN SULFATE MW: 500,000 PHARMACIA 17% S
\*: AVERAGE FOR 6 WELLS (BO) AVERAGE FOR 2 WELLS FOR OTHER VALUES
ELISA D3-D4 CARRIED OUT 24 H AFTER SAMPLING
ND: CANNOT BE DOSED BECAUSE OF THE ANTICOAGULATING ABILITY OF SULFATE D DEXTRAN

TABLE 5

STUDY OF THE EFFECTS OF THE ADDITION OF SULFATED POLYMERS TO THE PRODUCTION
MEDIA FOR FACTOR VIII DELTA 2 CLONE CHO TG 2307-11-3
EFFECTS OF HYDROXYETHYLSTARCH SULFATED OF MW 200,000 Da AT 3.76% AND 13.1% OF S
AND OF SIGMA LOW VISCOSITY CARBOXYMETHYLCELLULOSE

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| MEM HT 10% FCS ND | 3100 | 40200 | 1370 | 20000 | 740 | 18500 | 810 | 13500 |
| H/I HUM INS 4 mg/L + 2 U vWFrec CNTS/ML | 1300 | 18200 | 1530 | 30800 | 940 | 22400 | 1600 | 21000 |
| H/I HUM INS 4 mg/L | 170 | 3200 | 124 | 1100 | 25 | 760 | 260 | 1900 |
| H/I HUM INS 4 mg/L + 100 mg/L CMC | ND | 5500 | ND | 1400 | ND | 970 | ND | 1820 |
| H/I HUM INS 4 mg/L + 500 mg/L CMC | ND | 4600 | ND | 1900 | ND | 850 | ND | 2100 |
| H/I HUM INS 4 mg/L + 1000 mg/L CMC | ND | 4400 | ND | 2200 | ND | 1200 | ND | 2350 |
| H/I HUM INS 4 mg/L + 100 mg/L-HESS 13.1% | ND | 8700 | ND | 10300 | ND | 5800 | ND | 5700 |
| H/I HUM INS 4 mg/L + 500 mg/L-HESS 13.1% | ND | 12800 | ND | 21900 | ND | 9900 | ND | 10500 |
| H/I HUM INS 4 mg/L + 1000 mg/L-HESS 13.1% | ND | 11900 | ND | 18000 | ND | 11500 | ND | 12800 |
| H/I HUM INS 4 mg/L + 100 mg/L-HESS 3.76% | ND | 7500 | ND | 4900 | ND | 2100 | ND | 2240 |
| H/I HUM INS 4 mg/L + 500 mg/L-HESS 3.76% | ND | 8300 | ND | 11000 | ND | 5000 | ND | 4740 |
| H/I HUM INS 4 mg/L + 1000 mg/L-HESS 3.76% | ND | 8200 | ND | 14200 | ND | 6700 | ND | 5530 |

PASSAGE P19 AFTER THAWING AND P18 IN MEM HT FCS ND 701121
GROWTH (37) AND TEST FOR PRODUCTION (35C) IN 6-WELL PLATES NUNC
CHANGE OF MEDIUM EVERY 24 HOURS
HUMAN INS ELI LILLY 319KK9B
6-WELL PLATES NUNC
HYDROXYETHYLSTARCH SULFATE MW: 200,000 PFEIFER AND LANGEN 3.76 AND 13.1% S
CONCENTRATED vWFrec CNTS AT 63.7 U/ML OF 11/12/89
ND: CANNOT BE DOSED BECAUSE OF THE ANTICOAGULATING ABILITY OF SULFATED POLYMERS
ELISA OF D4-D5: INCUBATION Ag 14 HOURS AT +20° C.

EXAMPLE 4

Other polymers and in particular, carboxymethylcellulose, hydroxyethylstarch sulfate (MW: 200,000) with 3.76 and 13.1% of sulfur were evaluated for their ability to influence the rate of expression of factor VIII delta 2 in a medium without serum and without factor von Willebrand and this was done relative to controls containing 10% bovine serum, 2 units/ml recombinant von Willebrand factor or neither serum nor von Willebrand.

The carboxymethylcellulose at the concentrations tested does not have a marked effect on the expression of factor VIII delta 2, whereas starch hydroxyethyl sulfate with 13% sulfur at concentrations of 0.5 and 1.0 g/l allows the accumulation in 24 hours of up to about 20 units of C: Ag/ml of factor VIII delta 2, that is to say about ⅔ of what is obtained during the same period in the presence of 2 units/ml of recombinant von Willebrand factor. The same polymer containing only 3.76% of sulfur has an effect on the expression of factor VIII delta 2 which is significantly less marked. This experiment confirms the usefulness of sulfated polysaccharides and reveals the importance of the degree of sulfation in the interaction of polymers with the molecule of factor VIII delta 2.

EXAMPLE 5

Study of the Effects of Sulfated Dextran on the Expression of Factor VIII

The study is carried out using the clone CHO TG 1566-3013 which expresses the molecule of complete factor VIII.

FIG. 1 shows the existence of a dose-effect of sulfated dextran (Pharmacia MW: 500,000) on the expression of factor VIII in 6-well plates.

It is observed that over 2 days of production, D4-D5 and D5-D6, the production of factor VIII is significantly increased relative to a control without sulfated dextran. A threshold is reached at 500 mg/l of sulfated dextran.

EXAMPLE 6

Comparison of the Effects of vWF and Sulfated Dextran (MW: 50,000) on the Expression of Factor VIII in a Chemically Defined Medium This study is carried out in a 1 l bioreactor (SGI). The clone CHO TG 1566-3013 which expresses the complete factor VIII is cultured on the support Cultispher-G at the concentration of 4 g/l (microporous beads of crosslinked bovine gelatin).

After a growth phase of 4 days in an Iscove medium containing 5% FCS, the influence of 3 different production media are tested:

a medium containing 5% FCS and containing neither vWF nor sulfated dextran (medium A)

a medium without FCS containing 1 UI vWF/ml (medium B)

a medium without vWF or FCS and containing 200 mg/l sulfated dextran (MW: 50,000) (medium C).

Figure 2:
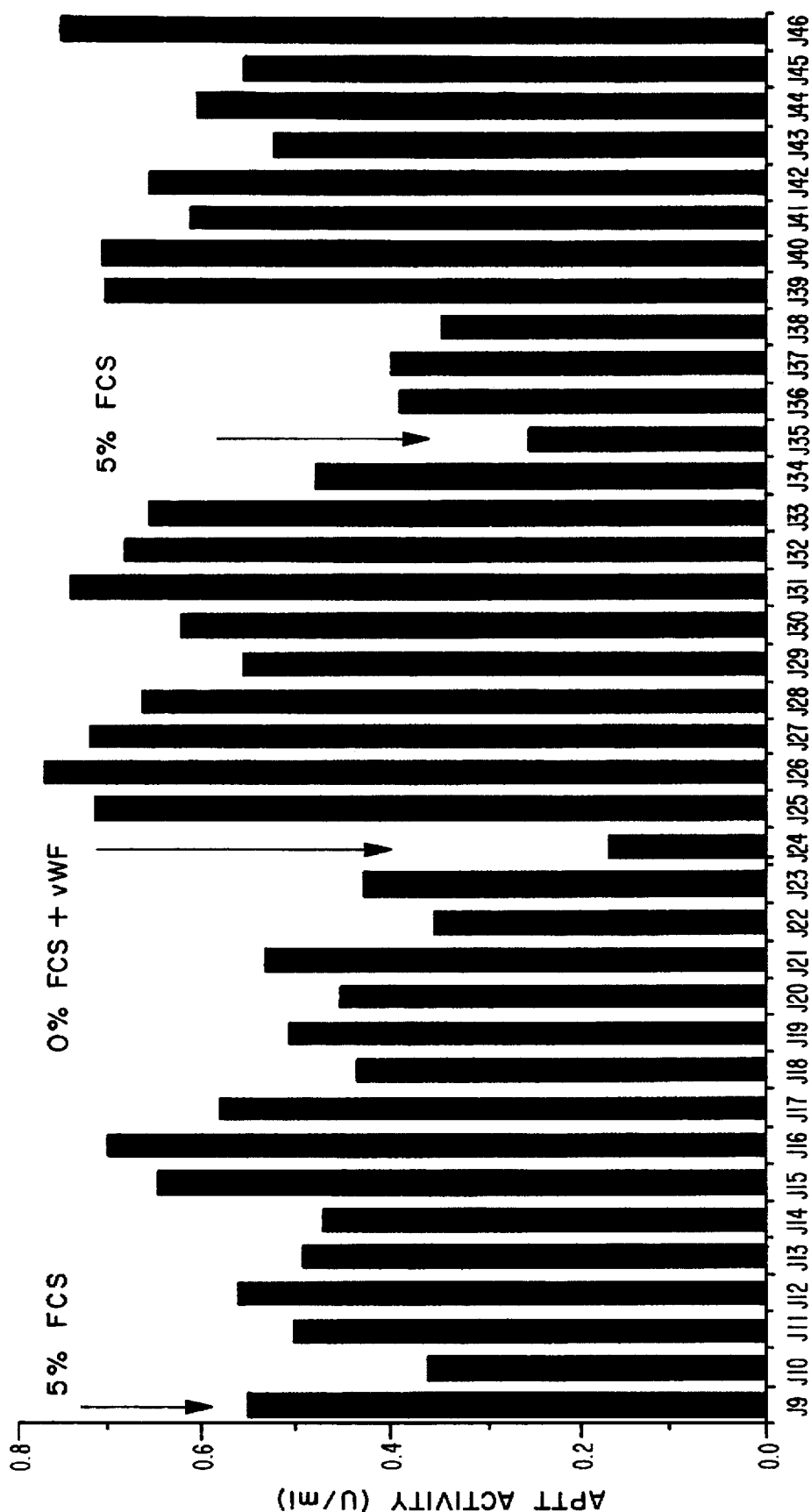
FIG. 2 shows factor VIII expression for cells cultured on medium with 5% FCS+200 mg/l sulfated dextran (MW:50,000).

The results are presented in FIG. 2.

The activity for factor VIII is expressed in units APTT/l of medium in a medium which does not contain sulfated dextran, and in the unit Cag in a medium which contains sulfated dextran (ELISA assay). The ratio between the assays APTT and ELISA is of the order of 1.2 to 1.4.

It is found that the productions achieved in medium B are higher than those achieved in medium A (680±67 U APTT/l against 502±96 U APTT/l). The productions achieved in medium C are comparable to those obtained in medium B.

In conclusion, it is clearly shown that sulfated dextran can be substituted for von Willebrand factor in order to increase the expression of factor VIII in a chemically defined medium.

We claim:

1. In a process for the preparation and separation of factor VIII or an analog of factor VIII, the process comprising culturing mammalian eukaryotic cells which produce and secrete said factor VIII or analog of factor VIII, said mammalian eukaryotic cells having incorporated an expression vector containing a gene encoding for said factor VIII or analog of factor VIII, proviso they are not chosen among: Vero, Hela, WI38, BHK, CHO, COS-7 and MDCK, said mammalian cells expressing the molecule of factor VIII or analog of factor VIII in a continuous manner, and then separating said factor VIII or analog of factor VIII wherein the improvement comprises culturing the mammalian cells in a serum free culture medium and free of Von Willebrand factor, supplemented with at least one derivative which is a sulfated polysaccharide of molecular weight between 5,000 and 700,000 and a degree of sulfation of 0.5% to 18% by weight of sulfur, in an amount sufficient to provide an enhancement of factor VIII or analog of factor VIII production compared with culturing the mammalian cells in a medium without said sulfated polysaccharide.

2. The process of claim 1 wherein the sulfated dextran preferably has a degree of sulfation of 10% to 18%.

3. The process of claim 1, wherein the sulfated polysaccharide is chosen from the group consisting of heparin, sulfated dextran and hydroxy ethylstarch.

4. The process claim 1, wherein the analog of factor VIII which is prepared is factor VIII delta 2.

5. In a process for the preparation and separation of factor VIII or an analog of factor VIII, the process comprising culturing mammalian eukaryotic cells which produce and secrete said factor VIII or analog of factor VIII, said mammalian eukaryotic cells having incorporated an expression vector containing a gene encoding for said factor VIII or analog of factor VIII said cells being chosen among recombinant Veto, Hela, WI38, BHK, CHO, COS-7 and MDCK cells which express the molecule of factor VIII or analog of factor VIII in a continuous manner, and then separating said factor VIII or analog of factor VIII, wherein the improvement comprises culturing the mammalian cells in a serum free culture medium and free of Von Willebrand factor, supplemented with at least one derivative which is a sulfated polysaccharide of molecular weight between 5,000 and 700,000 and a degree of sulfation of 65% to 18% by weight of sulfur, in an amount sufficient to provide an enhancement of factor VIII or analog of factor VIII production compared with culturing the mammalian cells in a medium without said sulfated polysaccharide proviso that said sulfated polysaccharide is not chosen among heparin, sulfated dextran and hydroxyethylstarch sulfate of molecular weight between 5000 and 700,000 and a degree of sulfation of 0.5% to 18% by weight of sulfur.

6. The process of claim 5, wherein the analog of factor VIII which is prepared is factor VIII delta 2.

7. The process of claim 5, wherein the cells in culture are recombinant CHO cells which express the molecule of factor VIII or analog of factor VIII in a continuous manner.

8. A process for the preparation and separation of factor VIII or an analog of factor VIII, the process comprising culturing mammalian eukaryotic cells which produce and secrete said factor VIII or analog of factor VIII, said mammalian eukaryotic cells having incorporated an expression vector containing a gene encoding for said factor VIII or analogue of factor VIII, proviso though they are not chosen among: Vero, Hela, WI38, BHK, CHO, COS-7, MDCK, said mammalian cells expressing the molecule factor VIII or analog of factor VIII in a continuous manner, and then separating said factor VIII or analog of factor VIII wherein the improvement comprises culturing the mammalian cells in a serum free culture median and free of Von Willebrand factor, supplemented with a sulfated polysaccharide selected from the group consisting of heparin, sulfated dextran, and hydroxyethyl starch, in an amount sufficient to provide an enhancement of factor VIII or analog of factor VIII production compared with culturing the mammalian cells in a medium without said supplement.

* * * * *

UNITED STATES PATENT AND TRADEMARK OFFICE
CERTIFICATE OF CORRECTION

PATENT NO.: 5,707,832
DATED: January 13, 1998
INVENTOR(S): Mignot et al.

It is certified that error appears in the above-identified patent and that said Letters Patent is hereby corrected as shown below:

In item [57], the Abstract, please delete the space between the two paragraphs, thereby making it into one paragraph.

In column 12, claim 5, line 32, delete "a degree of sulfation of 65% to 18%" and insert -- a degree of sulfation of 0.5% to 18% --.

Signed and Sealed this

Twenty-ninth Day of May, 2001

Attest:

NICHOLAS P. GODICI

*Attesting Officer*  *Acting Director of the United States Patent and Trademark Office*